US012734292B2

(12) United States Patent
Pizzochero et al.

(10) Patent No.: US 12,734,292 B2
(45) Date of Patent: Sep. 15, 2026

(54) BALL JOINT-STYLE, NON-FIXED COUPLING BETWEEN A PUSHER PLATE AND PLUNGER IN A SYRINGE BARREL

(71) Applicant: Becton, Dickinson and Company, Franklin Lakes, NJ (US)

(72) Inventors: Alessandro Pizzochero, Chelmsford, MA (US); Mark Wood, Sterling, MA (US); Nicholas Anderson, Whitman, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 482 days.

(21) Appl. No.: 18/259,649

(22) PCT Filed: Dec. 28, 2021

(86) PCT No.: PCT/US2021/065408
§ 371 (c)(1),
(2) Date: Jun. 28, 2023

(87) PCT Pub. No.: WO2022/147054
PCT Pub. Date: Jul. 7, 2022

(65) Prior Publication Data

US 2024/0066216 A1 Feb. 29, 2024

Related U.S. Application Data

(60) Provisional application No. 63/133,764, filed on Jan. 4, 2021.

(51) Int. Cl.

| | |
|---|---|
| ***A61M 5/145*** | (2006.01) |
| ***A61M 5/142*** | (2006.01) |

(Continued)

(52) U.S. Cl.
CPC ...... *A61M 5/1452* (2013.01); *A61M 5/14248* (2013.01); *A61M 5/3129* (2013.01);
(Continued)

(58) Field of Classification Search
CPC ........... A61M 5/14248; A61M 5/1452; A61M 5/3129; A61M 5/31513; A61M 5/31515;
(Continued)

(56) References Cited

U.S. PATENT DOCUMENTS

| | | | |
|---|---|---|---|
| 6,206,859 | B1 | 3/2001 | Niedospial, Jr. et al. |
| 2012/0022453 | A1 | 1/2012 | Yodfat et al. |

(Continued)

FOREIGN PATENT DOCUMENTS

| | | | |
|---|---|---|---|
| CN | 102378638 | A | 3/2012 |
| CN | 217660959 | U | 10/2022 |

(Continued)

OTHER PUBLICATIONS

International Search Report dated May 2, 2022, which issued in the corresponding PCT Patent Application No. PCT/US2021/065408.

*Primary Examiner* — John Kim
(74) *Attorney, Agent, or Firm* — Dickinson Wright PLLC

(57) ABSTRACT

A fluid delivery device has a syringe barrel with reservoir chamber for fluid, a plunger that translates along a longitudinal axis to expel fluid, and a pusher dimensioned to translate within the barrel and coupled to a drive mechanism to controllably contact and move the plunger. The pusher contacts the plunger at its mechanical center to reduce tilt in the plunger. Contact faces of the pusher and plunger cooperate as a ball joint to minimize non-axial forces on the plunger face. The pusher can have a protrusion of various lengths extending toward and being at least partially received in a recess of various depths in the plunger. The pusher is rigidly connected to a drive mechanism for anti- (Continued)

rotation. The pusher can have scalloped edges for air venting, and apertures for cooperating with protrusions on the drive mechanism to prevent bottoming out the plunger when filling.

17 Claims, 22 Drawing Sheets

(51) Int. Cl.
*A61M 5/31* (2006.01)
*A61M 5/315* (2006.01)

(52) U.S. Cl.
CPC .... *A61M 5/31513* (2013.01); *A61M 5/31515* (2013.01); *A61M 2005/3123* (2013.01); *A61M 2005/31518* (2013.01); *A61M 2005/3152* (2013.01)

(58) Field of Classification Search
CPC ........... A61M 2005/3123; A61M 2005/31518; A61M 2005/3152
See application file for complete search history.

(56) References Cited

U.S. PATENT DOCUMENTS

| | | | | |
|---|---|---|---|---|
| 2012/0136298 | A1 | 5/2012 | Bendix et al. | |
| 2012/0172817 | A1 | 7/2012 | Brueggemann et al. | |
| 2015/0105735 | A1 | 4/2015 | Zhou | |
| 2020/0238003 | A1 | 7/2020 | Yigal et al. | |
| 2022/0054740 | A1 * | 2/2022 | Wood ................ | A61M 5/31535 |

FOREIGN PATENT DOCUMENTS

| | | | |
|---|---|---|---|
| EP | 3 501 570 | A1 | 6/2019 |
| EP | 3 656 418 | A1 | 5/2020 |
| JP | 2013-503672 | A | 2/2013 |
| JP | 2015228972 | A | 12/2015 |
| JP | 2018-047239 | A | 3/2018 |
| JP | 2020-518392 | A | 6/2020 |
| WO | 2019199901 | A1 | 10/2019 |
| WO | 2020104872 | A1 | 5/2020 |

* cited by examiner

BALL JOINT-STYLE, NON-FIXED COUPLING BETWEEN A PUSHER PLATE AND PLUNGER IN A SYRINGE BARREL

BACKGROUND

Field

Illustrative embodiments relate generally to a pusher, driven by an extending mechanism, and a plunger arranged in a syringe barrel to minimize the effects of non-axial forces on the movement of the plunger face in a direction perpendicular to the reservoir axis.

Description of Related Art

Currently, infusion devices for medication delivery are commercially available that include extra high precision pumps for critical applications such as accurate insulin delivery to Type 1 diabetes patients. These infusion devices nonetheless cannot maintain the desired accuracy for delivery of highly consistent doses throughout the entire life cycle of the infusion device. A need exists for a wearable, low-cost drug delivery pump with high delivery precision throughout its life cycle.

SUMMARY

Problems are overcome, and additional advantages are realized, by illustrative embodiments described herein.

A fluid delivery device is provided that has a syringe barrel with reservoir chamber that can contain fluid and a plunger that translates within the chamber along a longitudinal reservoir axis thereof to expel fluid from the chamber and out of the syringe barrel via an outlet, the fluid delivery device comprising: a pusher dimensioned to translate within the barrel, the plunger having a front face directed toward the outlet and a rear face directed toward a front face of the pusher; and an extending mechanism coupled to a rear face of the pusher to controllably translate the pusher within the chamber along the longitudinal reservoir axis. The extending mechanism is configured to extend the front face of the pusher to abut at least a portion of the rear face of the plunger to move the plunger.

In accordance with aspects of example embodiments, the pusher is configured as a plate and the extending mechanism is connected to a point on the rear face of the pusher that is centered with respect to the longitudinal reservoir axis.

In accordance with aspects of example embodiments, the perimeter of the syringe barrel, the plunger and the pusher have same cross-sectional shape. For example, the cross-sectional shape can be chosen from elliptical and circular.

In accordance with aspects of example embodiments, the extending mechanism comprises telescopic nested screws rotated controllably to extend and retract the pusher. The rear face of the pusher is connected to a distal end of one of the nested screws. The distal end of the screw comprises an anti-rotation feature configured to cooperate with another anti-rotation feature provided on the rear face of the pusher. For example, the anti-rotation feature of the screw is a protrusion of selected shape, and the anti-rotation feature on the pusher is an indent having the selected shape to receive the protrusion.

In accordance with aspects of example embodiments, the rear face of the plunger is flat, and a majority of the front face of the pusher can abut the rear face of the plunger when the extending mechanism is moving the plunger via the pusher.

In accordance with aspects of example embodiments, the front face of the pusher has a protrusion extending distally toward the rear face of the plunger. For example, the protrusion has a half-spherical shape.

In accordance with aspects of example embodiments, the rear face of the plunger has a recess for receiving at least a portion of the protrusion.

In accordance with aspects of example embodiments, the protrusion and the recess can be configured to cooperate together as a mechanical ball joint to reduce tilt of the plunger that could occur when translated by the extending mechanism driving pusher into the plunger.

In accordance with aspects of example embodiments, an innermost wall of the recess has a surface character that is flat, or contoured to accommodate at least part of the protrusion.

In accordance with aspects of example embodiments, the recess has a depth dimensioned to accommodate the full length of the protrusion to achieve direct contact of the front face of the pusher with the rear face of the plunger.

In accordance with aspects of example embodiments, the recess has a depth dimensioned to accommodate only a portion of the full length of the protrusion such that a gap exists between the front face of the pusher when driven into the rear face of the plunger by the extending mechanism.

In accordance with aspects of example embodiments, the pusher comprises indents along at least a portion of its perimeter for air venting.

In accordance with aspects of example embodiments, the plunger has extensions from its rear face that form a receptacle to receive the pusher.

In accordance with aspects of example embodiments, the pusher comprises an aperture to rigidly receive one of the nested screws. The distal end of the screw protrudes from the front side of the pusher. The plunger comprises a recess to receive the protruding distal end therein.

In accordance with aspects of example embodiments, the plunger has a protrusion extending from its rear face toward the front face of the pusher. The protrusion contacts a point on the front face of the pusher that is centered with respect to the longitudinal reservoir axis.

In accordance with aspects of example embodiments, a contact is provided to at least one of the plunger and the pusher and operable to provide a contact signal when the plunger and the pusher contact each other.

In accordance with aspects of example embodiments, the pusher comprises holes extending from its front face to its rear face. A front face of the extending mechanism is provided with protrusions received in the holes on the pusher when the extending mechanism fully retracts the pusher.

Additional and/or other aspects and advantages of illustrative embodiments will be set forth in the description that follows, or will be apparent from the description, or may be learned by practice of the illustrative embodiments. The illustrative embodiments may comprise apparatuses having one or more of the above aspects, and/or one or more of the features and combinations thereof. The illustrative embodiments may comprise one or more of the features and/or combinations of the above aspects as recited, for example, in the attached claims.

BRIEF DESCRIPTION OF THE DRAWINGS

The above and/or other aspects and advantages of the illustrative embodiments will be more readily appreciated from the following detailed description, taken in conjunction with the accompanying drawings, of which.

Throughout the drawing figures, like reference numbers will be understood to refer to like elements, features and structures.

DETAILED DESCRIPTION OF ILLUSTRATIVE EMBODIMENTS

Figure 1A:
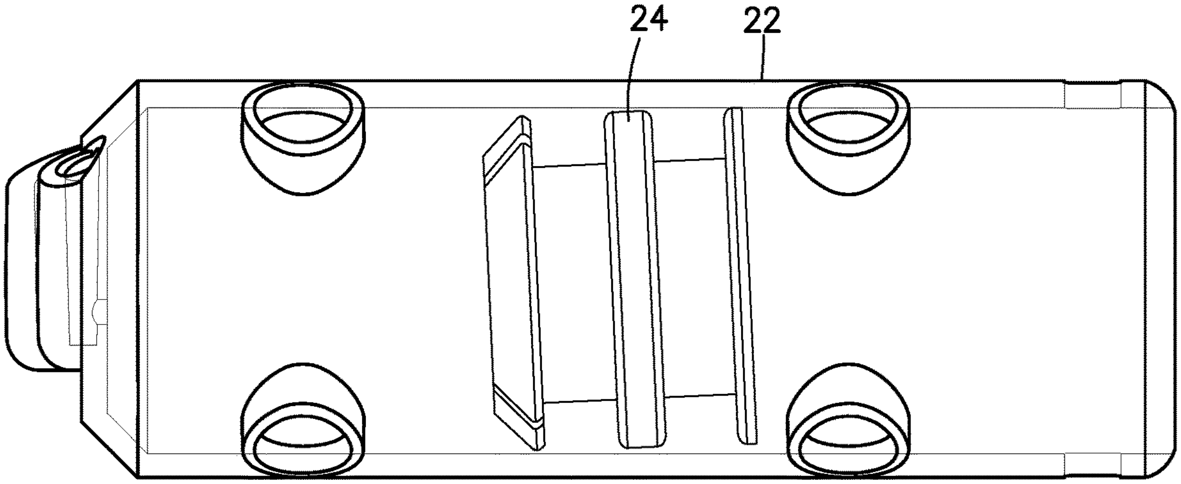
FIG. 1A is a side view of a barrel-type reservoir and plunger for use in an example fluid delivery device such as a syringe-type infusion device and constructed in accordance with an example embodiment.

Reference will now be made in detail to illustrative embodiments, which are depicted in the accompanying drawings. The embodiments described herein exemplify, but do not limit, the illustrative embodiments by referring to the drawings.

A common feature of the afore-mentioned existing infusion devices is the use of a screw-type drive mechanism for a plunger inside the infusion device's reservoir. Often, the interface of the plunger with the drive mechanism causes non-axial forces on the movement of the plunger face in a direction perpendicular to the longitudinal reservoir axis, which negatively impacts dose accuracy of the infusion pump.

Figure 1C:
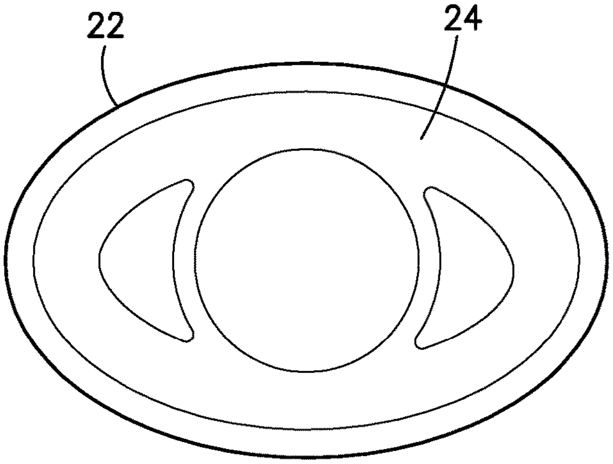
FIGS. 1B and 1C are perspective side and end views, respectively, of the reservoir and plunger shown in FIG. 1A.
Figure 1B:
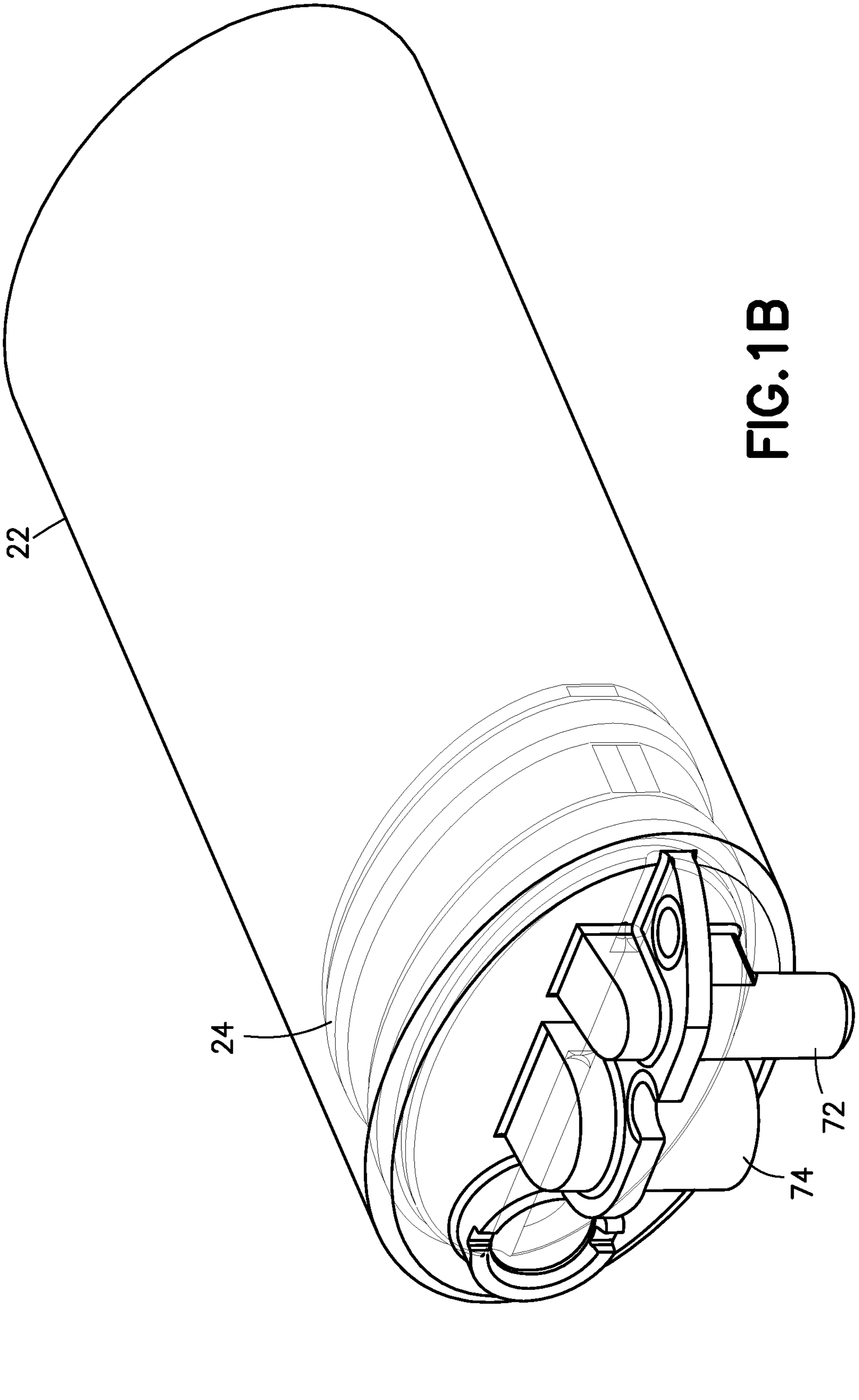

FIG. 1A is a side view of a barrel-type reservoir and plunger for use in an example fluid delivery device such as a syringe-type infusion device and constructed in accordance with an example embodiment. As shown in FIG. 1A, the plunger 24 can be potentially subjected to non-axial forces that cause a possible tilt of the plunger along a longitudinal axis of the reservoir 22. This misalignment of the plunger 24 with respect to the longitudinal axis and side walls of the reservoir 22 can cause dose inaccuracies as well as increased load on the pump motor operating the drive mechanism to move the plunger. As shown in FIGS. 1B and 1C, which are perspective side and end views, respectively, of the reservoir 22 and plunger 24 shown in FIG. 1A, the barrel-type reservoir and plunger can each have an elliptical cross-section. For an elliptical cross-section, there are also different contributions to error from either axis of the reservoir's cross-section when the plunger is tilted from non-axial forces.

The present disclosure provides a technical solution to the technical problem of improving dose accuracy of an infusion device by minimizing these non-axial forces on the movement of the plunger. Example embodiments of the technical solution are described below in connection with syringe-type infusion devices having a barrel-type reservoir and a plunger that translates within the barrel to expel fluid therefrom. These example embodiments employ a novel configuration for coupling a pusher, driven by an extending drive mechanism, with a plunger in a barrel of a fluid delivery device to minimize the effects of non-axial forces on the movement of the plunger face in a direction perpendicular to the reservoir axis.

The technical solution described herein improves dose accuracy of infusion devices, and is particularly advantageous for improving dose accuracy of disposable, wearable, low-cost drug delivery devices where high delivery precision is required, because the novel configuration for coupling a pusher with a plunger that translates along a barrel-type reservoir of a syringe-type infusion device is highly effective without adding significant cost or complexity to the infusion device. In accordance with an aspect of example embodiments of the technical solution described herein, a drive mechanism 30 can be coupled to a pusher 60 that cooperates with the plunger 24.

The technical solution and example embodiments described herein are with reference to an example lead screw-type drive mechanism 30 comprising telescopic nested screws rotated controllably to extend the plunger 24 in a barrel directly, or directly extend a pusher 60 as described below that in turn contacts the plunger 24 to extend it. Example drive mechanisms comprising three or four stages of telescopic nested screws is described with reference to commonly owned PCT/US2021/046136, filed Aug. 16, 2021. Other types of drive mechanisms can be used such as the three stage telescopic nested screw-type drive mechanism described in commonly owned PCT/US2021/046184, filed Aug. 16, 2021. Existing two stage nested screw-type drive mechanisms can be used as well, although they are not as accurate as the three stage and four stage nested screw-type drive mechanisms described in the aforementioned commonly-owned patent applications.

Figure 2:
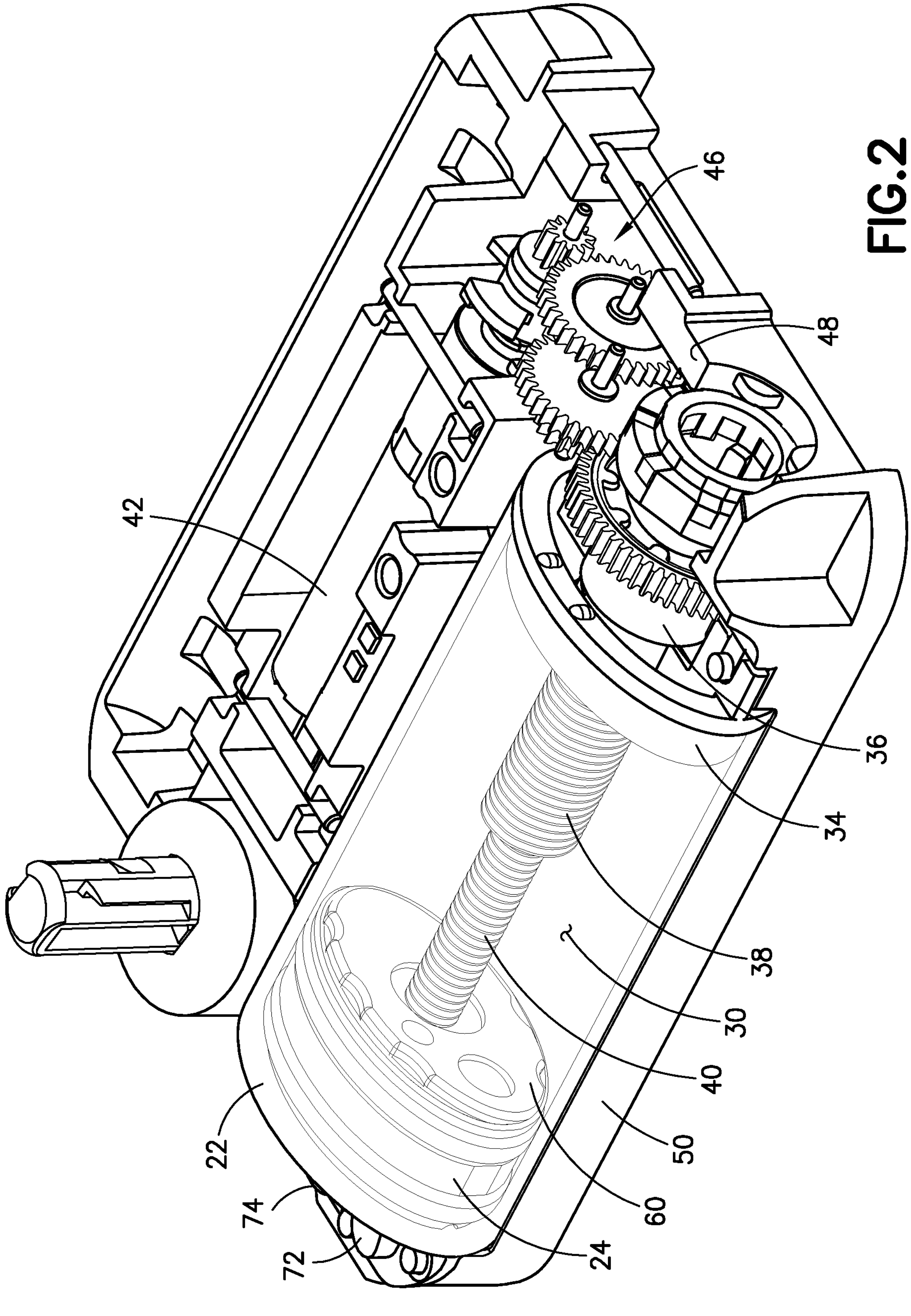
FIG. 2 is a top perspective view of an example fluid delivery device constructed in accordance with an example embodiment.

For example, FIG. 2 is a top perspective view of an example fluid delivery device 20 with its cover removed for clarity to depict a plunger drive mechanism 30 comprising a three stage telescopic nested screw-type drive mechanism coupled at a distal end thereof to the plunger 24 and coupled at a proximal end thereof to a gear train 46 and motor 42 assembly. The plunger 24 is provided within the reservoir 22 and configured to be controllably translated along the longitudinal axis of the reservoir 22 by the plunger drive mechanism 30 and motor 18 operation. The plunger drive mechanism 30 is shown fully extended in FIG. 2. It is to be understood that the motor 42 can control the plunger driver mechanism 30 to move the telescoping screw members 36, 38, and 40 incrementally from a fully retracted position to the fully extended position shown to deliver respective designated dose amounts of fluid from a fluid chamber portion 28 of the reservoir 22. The motor 42 and gear train 46 rotate an outermost drive screw 36 on the plunger driver mechanism 30. The gear train 46 can have different configurations. For example, the gear train 46 can also be in the form of a ratchet indexing mechanism or other indexing mechanism that precisely rotates the drive nut or outmost drive screw 36 by a mechanically controlled amount. The motor 42 and related gear train components 46 and the outermost drive screw 36 of the plunger drive mechanism 30 can be mounted with respect to each other via a mounting plate 48 or other mechanism secured to the baseplate 50. An inlet fluid path can be provided from a fill port (not shown) on the underside of baseplate 50 to an inlet port 74 of the reservoir 22 to allow filling of the reservoir prior to shipment, or by a user prior to using the fluid delivery device 10. The reservoir 22 has an outlet port 72 for providing fluid pumped from the reservoir 22 via the motor 42 and drive mechanism 30 to the patient via a catheter, for example. A gear anchor 34 is provided at a proximal end of the reservoir 22, and is stationary with respect to the reservoir 22. As shown in FIG. 2, the innermost screw 40 is shown coupled directly to a pusher 60 that contacts the rear face of the plunger 24.

Figure 3A:
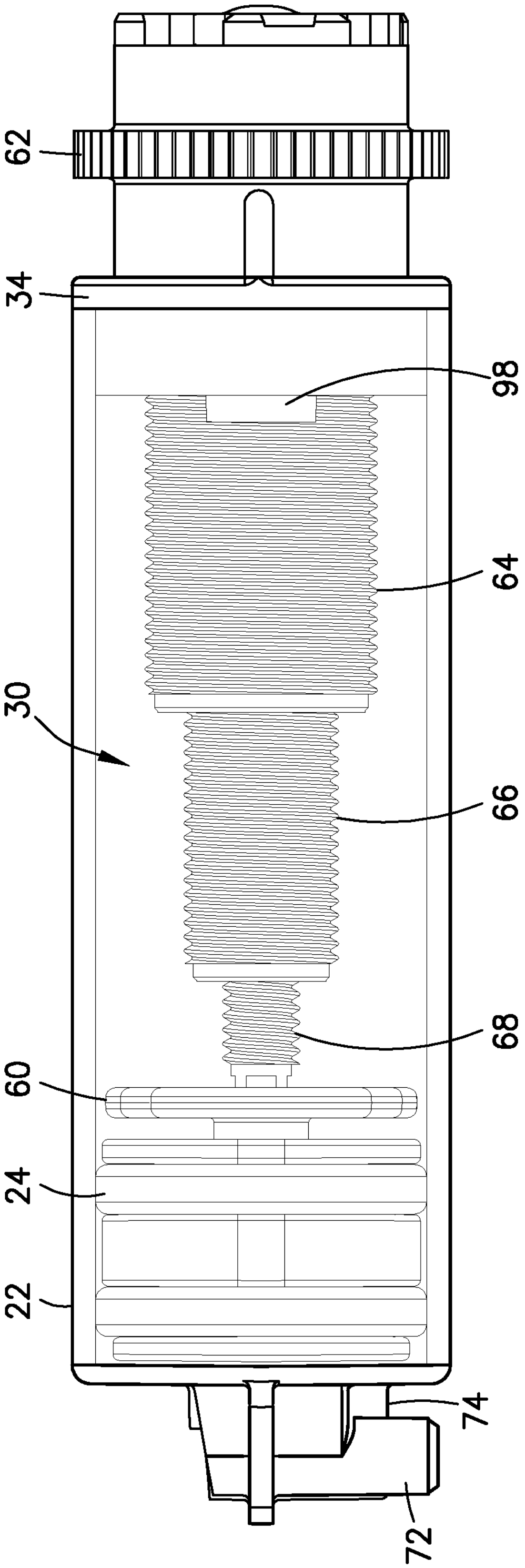
FIGS. 3A and 3B are side and perspective views, respectively, of a reservoir, plunger, pusher and an example drive mechanism of a fluid delivery device constructed in accordance with an example embodiment.
Figure 3B:
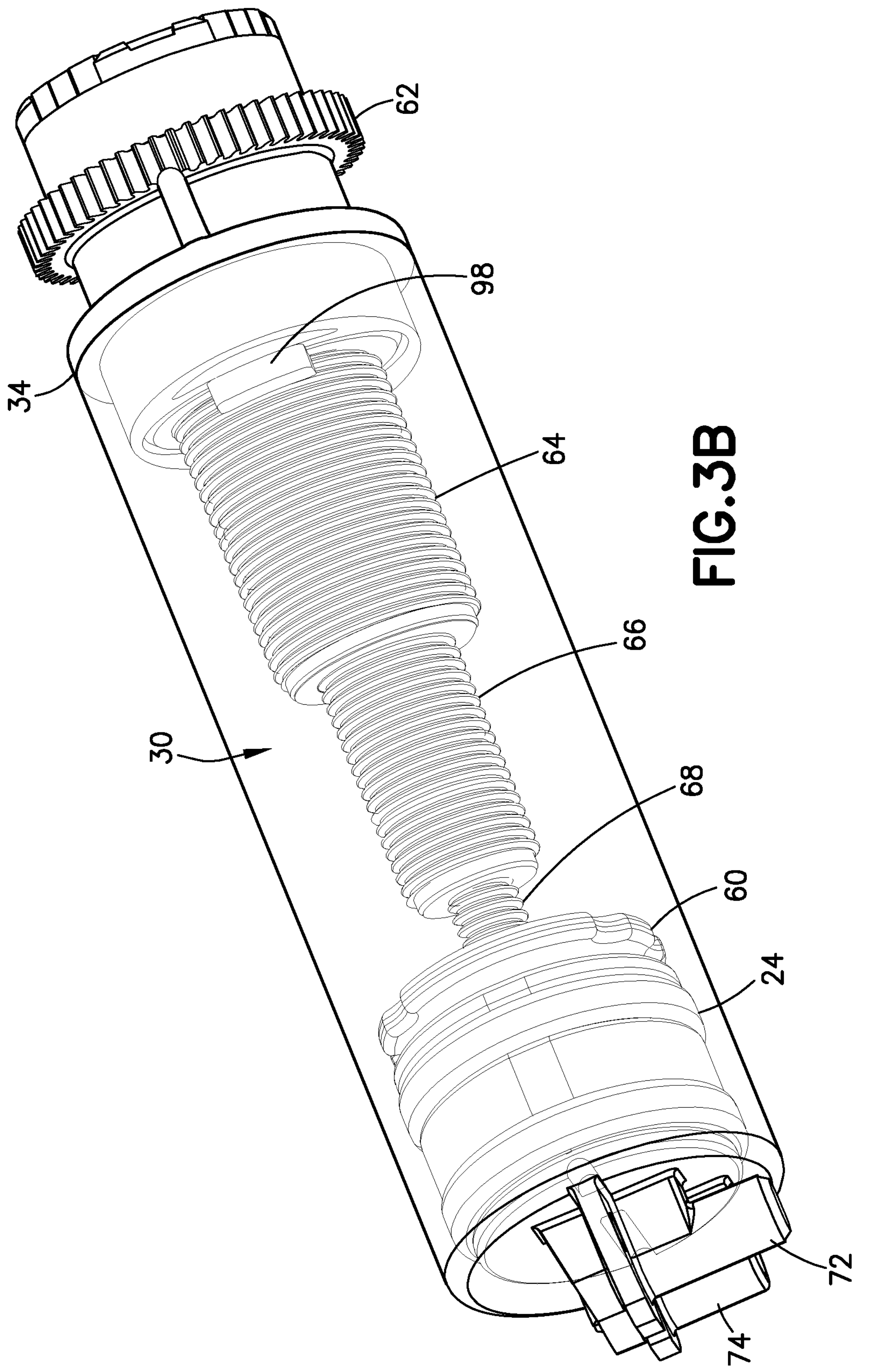

Another example pusher 60 and plunger 24 arrangement is depicted in FIGS. 3A and 3B. FIGS. 3A and 3B are side and perspective views, respectively, of a reservoir 22, plunger 24, pusher 60 and a four stage telescopic nested screw-type drive mechanism 30 of a fluid delivery device 20 constructed in accordance with another example embodiment. The four stage telescopic screw-type drive mechanism 30 comprises an outermost drive screw 62, a first sleeve screw 64, second sleeve screw 66 and an innermost screw 68.

As stated above, the drive mechanism 30 can have different configurations for controllably extending the plunger 24 and for optionally controlling, or manually, retracting the plunger. The drive mechanism 30 can have different configurations for directly, or indirectly (e.g., via a pusher 60), engaging with the plunger 24 to translate it along the longitudinal axis of the reservoir 22. In any event, the threaded members of the example drive mechanism 30 described herein employ nested telescoping screws of appropriate size and thread configuration to achieve a controlled movement of a syringe-barrel-type reservoir plunger 24. Screw-thread technology is well-defined and understood, and is capable of repeatable, powerful motion. When driven with an appropriate resolution-controlled motion by the motor 42, the nested screws (e.g., 38 and 40 in FIGS. 2 and 64, 66 and 68 in FIGS. 3A and 3B) can provide accurate movement under virtually all environmental conditions.

The technical solution and the various example embodiments described herein provide a novel configuration for coupling a pusher 60 to a plunger 24 in a syringe-type fluid delivery device 20 that can be deployed, for example, in infusion devices, syringes, injection pens, and any other device that uses a syringe-style mechanism to deliver fluid. The technical effect of the technical solution is minimization of transmission of any wobble from a drive mechanism 30 to the driven plunger 24, particularly when high precision motion is expected from the plunger.

Figure 6A:
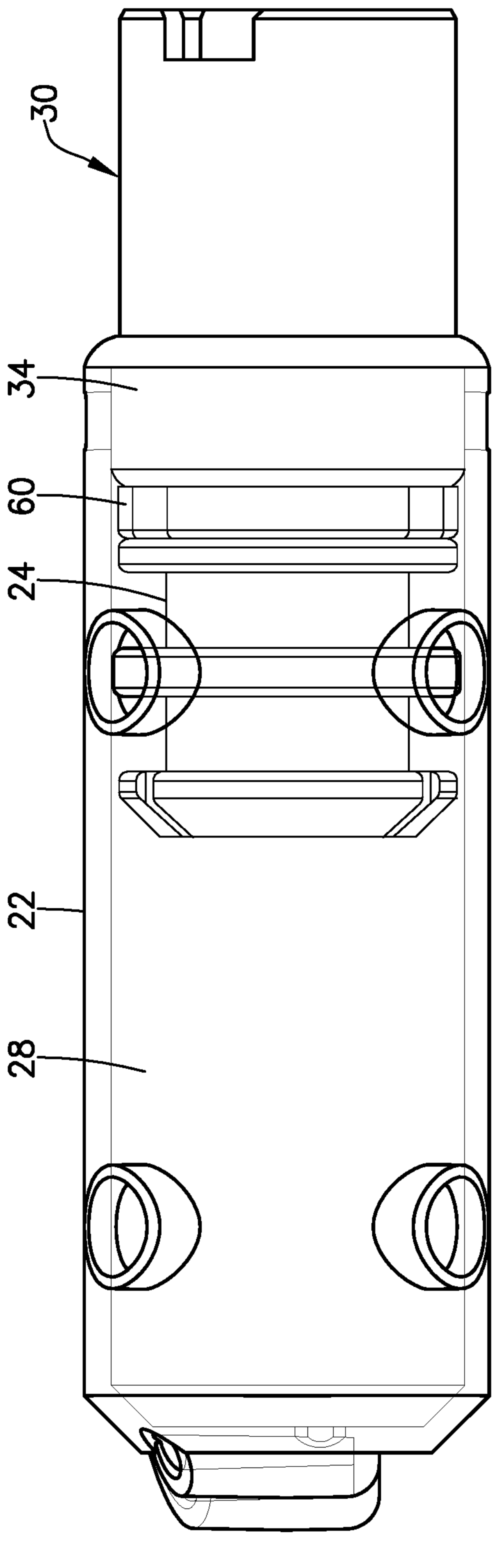
FIGS. 6A and 6B are respective side and cross-sectional side views of a fluid delivery device constructed in accordance with an example embodiment.
Figure 6B:
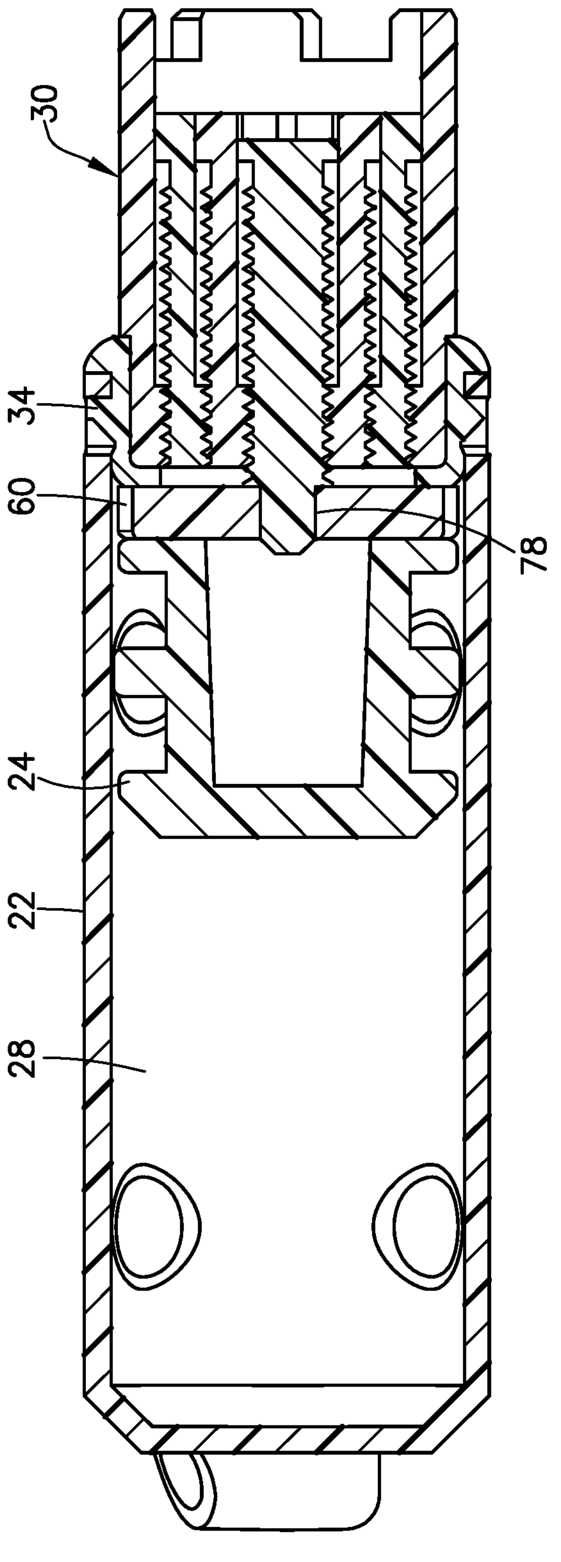

The front face of the pusher 60 directed to the distal end of the reservoir 22 in FIG. 2 is illustrated as a flat surface that has full face contact with the rear facing surface of the plunger 24, as described further below in connection with FIGS. 6A and 6B. In accordance with another example embodiment shown in FIGS. 3A and 3B, the pusher 60 has a dome-like or half-spherical protrusion 76 extending from its front face that abuts only part of the a rear facing surface of the pusher 24, as described further below in connection with FIGS. 4A, 4B and 4C. Another configuration for coupling the pusher 60 and plunger 24 is described below with reference to FIGS. 7A and 7B wherein the plunger has a half-spherical protrusion 86.

Figure 4A:
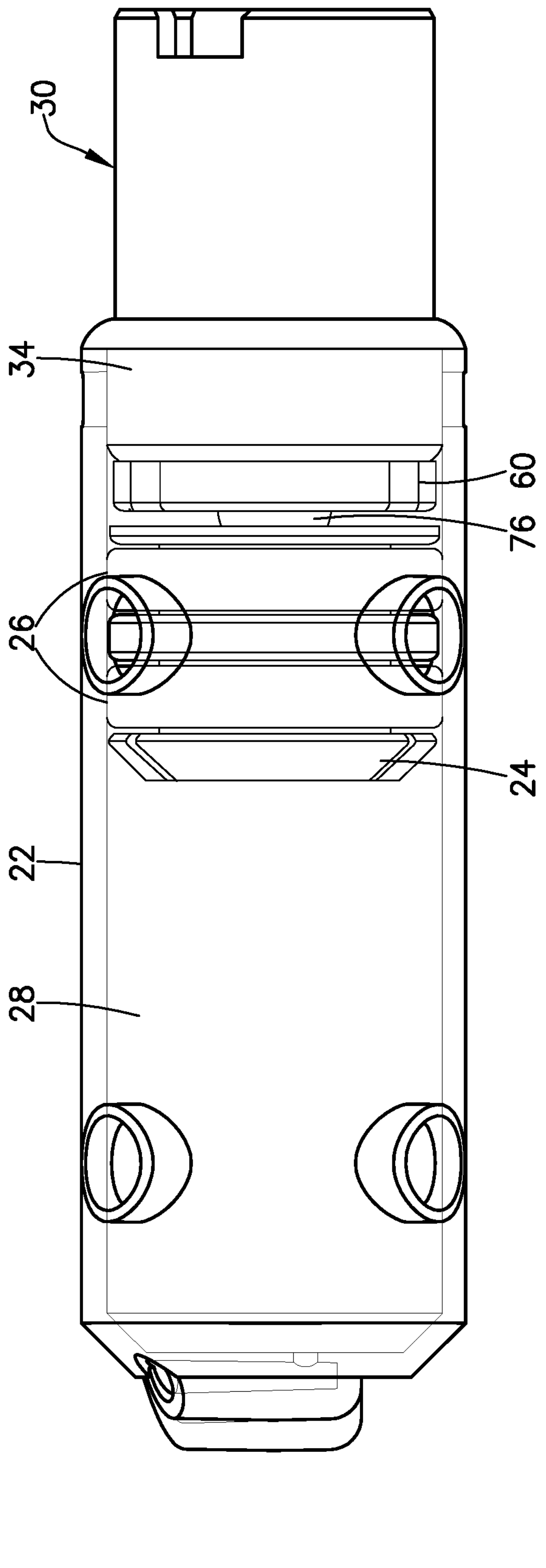
FIG. 4A is a side view of a syringe-type infusion device with barrel-type reservoir, plunger and pusher constructed in accordance with an example embodiment.
Figure 4B:
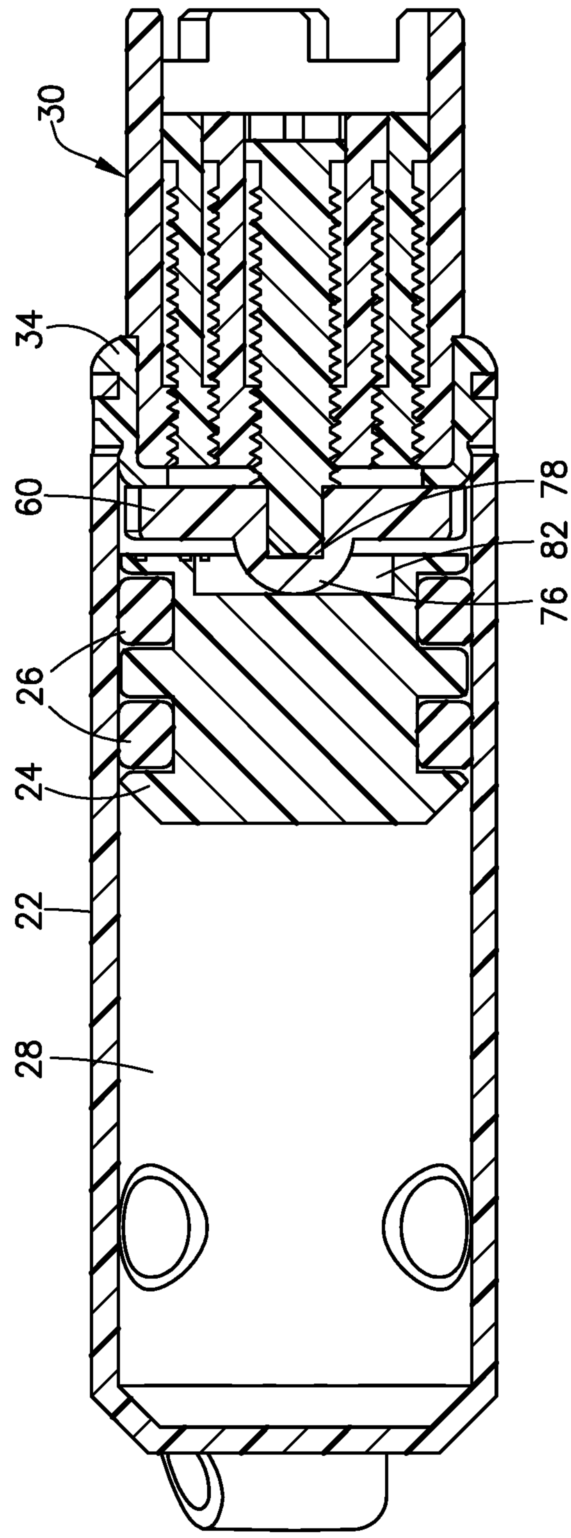
FIGS. 4B and 4C are cross-section side views of the syringe-type infusion device shown in FIG. 4A with an example drive mechanism shown, respectively, fully retracted and partially extended.
Figure 4C:
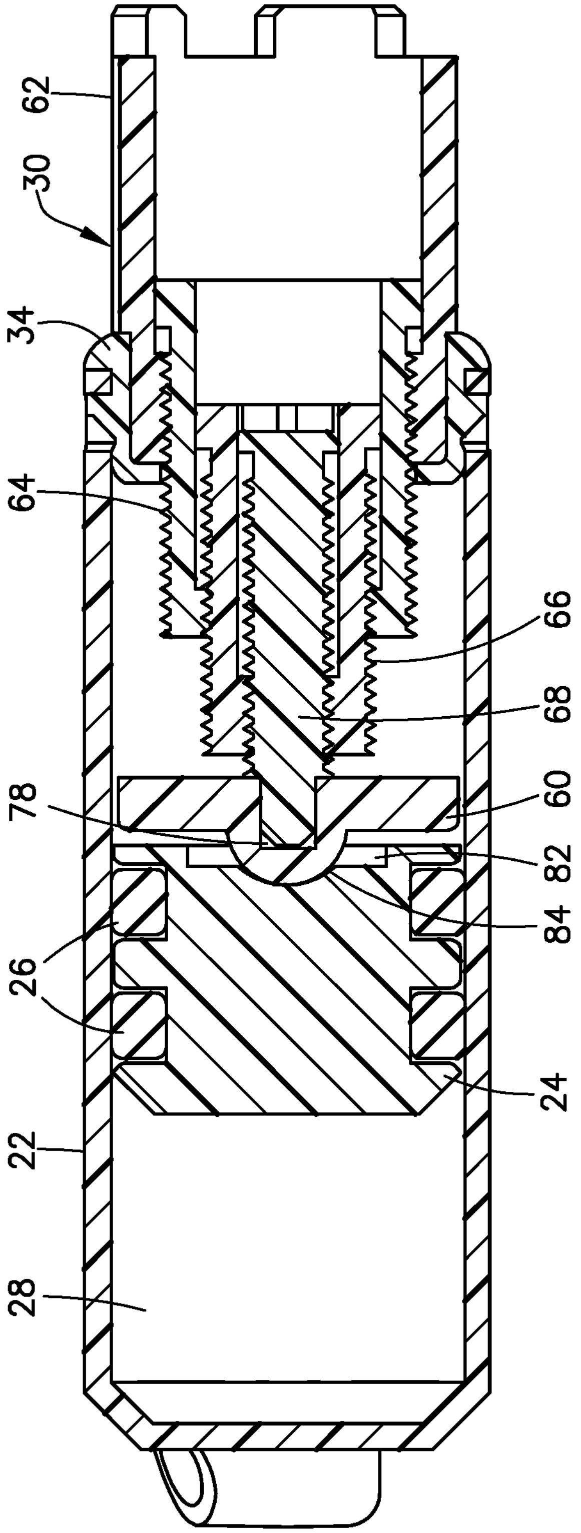

Reference is now made to the example embodiment in FIGS. 4A, 4B and 4C. FIG. 4A is a side view of a syringe-type infusion device with barrel-type reservoir 22, plunger 24 and pusher 60 constructed in accordance with the example embodiment. FIGS. 4B and 4C are cross-section views of the syringe-type infusion device shown in FIG. 4A with a four stage telescopic nested screw-type drive mechanism shown, respectively, fully retracted and partially extended. FIG. 4C depicts the recess 82 with an innermost wall having a contour or pocket recess 84 for accommodating at least part of the protrusion 76, and FIG. 4B illustrates the innermost wall of the recess 82 as flat, for illustrative purposes. The pusher 60 is illustrated as having a recess on its rear face for receiving the distal end of the innermost screw 68 of the drive mechanism 30. For example, the pusher 60 can be configured with a plate of sufficient thickness to accommodate a recess or detent 78 that is rigidly fixed to a key feature of the mechanism, which in this example embodiment can be a square key 80 or other key shape at the front of the smallest, inner telescoping screw 68. The front face of the pusher 60 is provided with a dome-like or half-spherical protrusion 76.

With continued reference to FIGS. 4A, 4B and 4C, the dome-like or half-spherical protrusion 76 on the front face of the pusher mates with or at least partially contacts the rear face of the plunger 24. Further, the pusher 60 circumference or perimeter is sized to be slightly smaller than the inner circumference or perimeter of the barrel-type reservoir 22 it is riding in so as to keep the center of the drive mechanism 30, such as a set of telescoping screws, as close as possible to the axis of the reservoir 22.

Figure 4D:
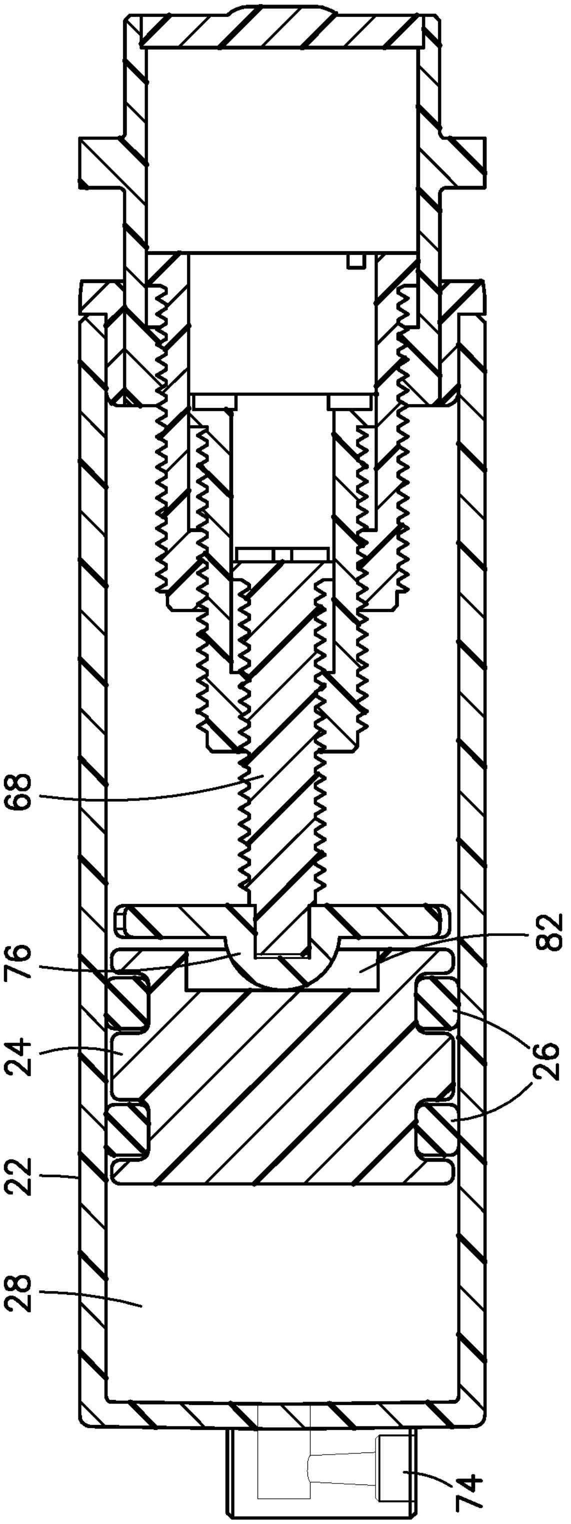
FIGS. 4D, 4E and 4F are cross-section side views of the syringe-type infusion device shown in FIG. 4A showing respective example lengths of a protrusion on the pusher and corresponding example depths of a recess in the plunger.
Figure 4E:
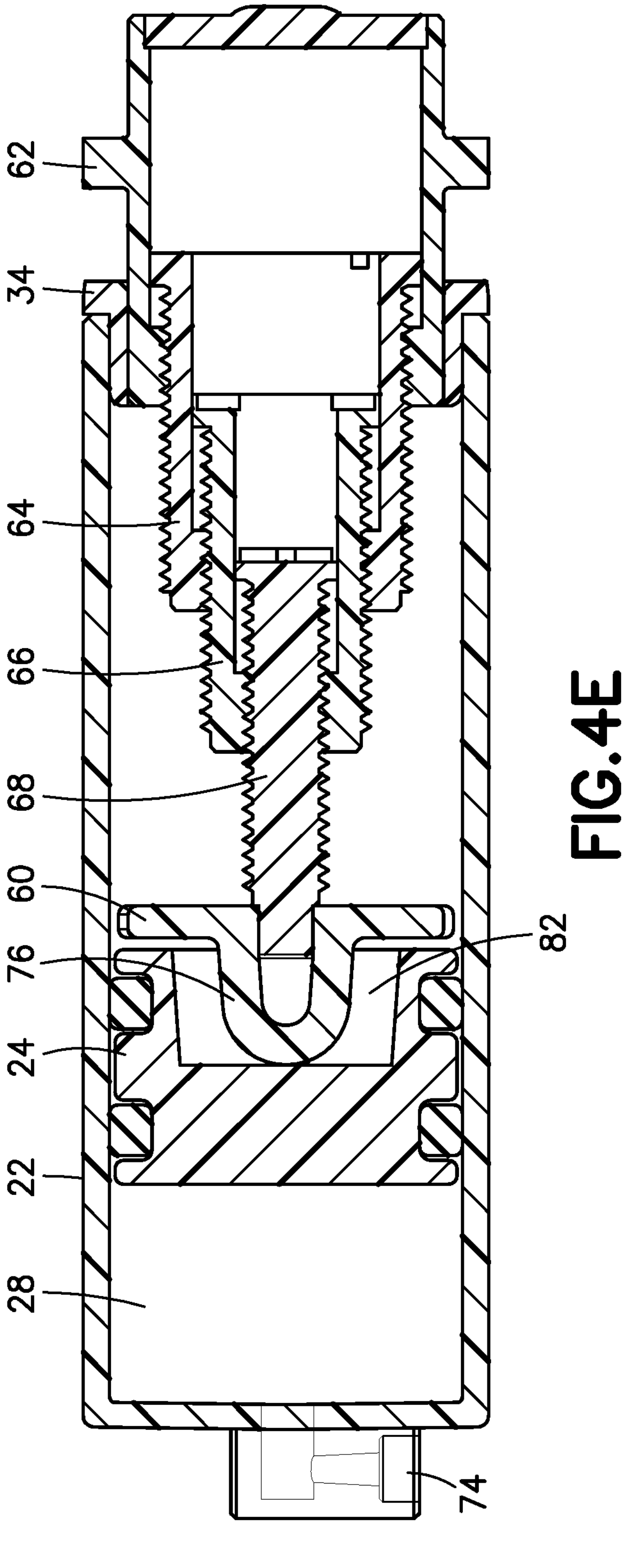
Figure 4F:
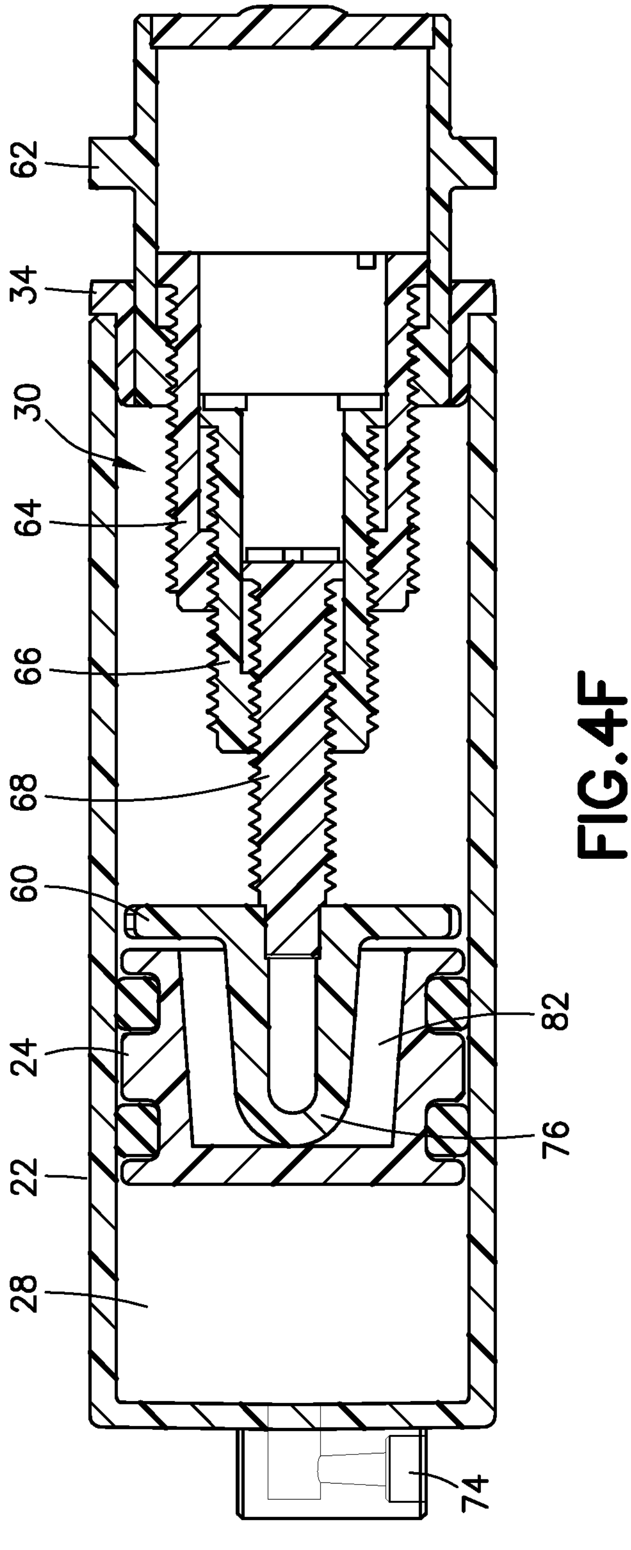
Figure 5:
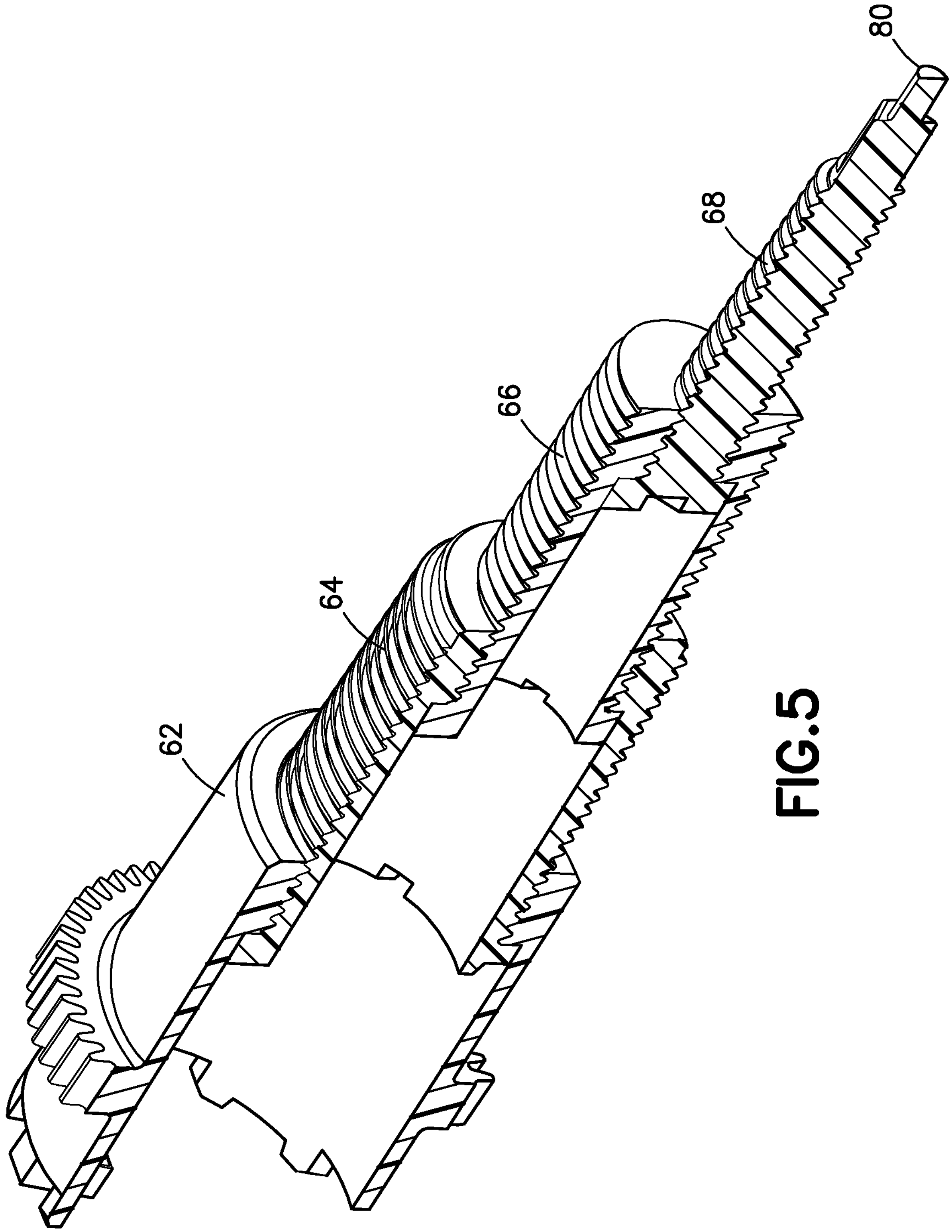
FIG. 5 is a perspective view of the example drive mechanism shown in FIGS. 4A through 4F.

The plunger 24 in the syringe barrel-type reservoir is understood to be the component that moves, or is moved by, the fluid. The plunger 24 can have a simple flat rear face to mate with the domed pusher, or can have a recess 82 configured to mate tangentially with the dome feature 76 on the pusher 60 as shown in FIGS. 4D, 4E and 4F. The pusher protrusion 76 can be dimensioned to minimize induced frictional and non-axial forces imparted onto the plunger 24. As shown in FIG. 4D, the pusher 60 is configured to have a plate portion surrounding the protrusion and having a perimeter dimensioned to be slightly smaller than the inner circumference of the reservoir 22. The rear side of the pusher 60 has a detent or a recess 78 that is similarly shaped to receive a keying feature 80 of the innermost screw of a drive mechanism 30, as shown in FIG. 5, to prevent relative rotation of the pusher and innermost screen. The recess 78 can extend longitudinally toward the front face of the pusher 60 and axially toward the internal distal end of the protrusion 76. As shown in FIGS. 4D, 4E and 4F, the length of the protrusion 76 and associated depth of the recess 82 can vary, for example, from a relatively shallow design (FIG. 4D), to a medium length design wherein the protrusion 76 extends into a plunger recess 82 ending at a medial point along the plunger 24 between its two O-tings 26 (FIG. 4E), to a longer length design wherein the protrusion 76 extends into a plunger recess 82 ending at the distal end of the plunger 24.

Figure 4H:
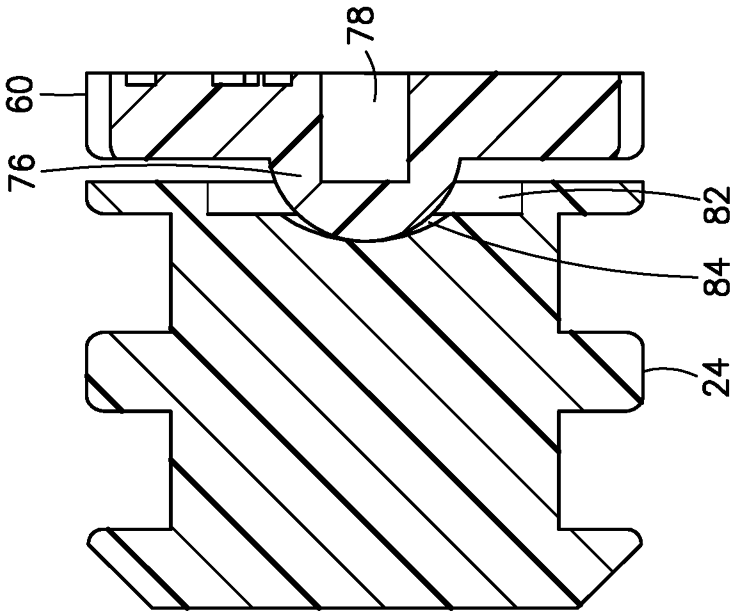
FIGS. 4G and 4H are respective cross-section side views of an example plunger and pusher constructed in accordance with example embodiments.
Figure 4G:
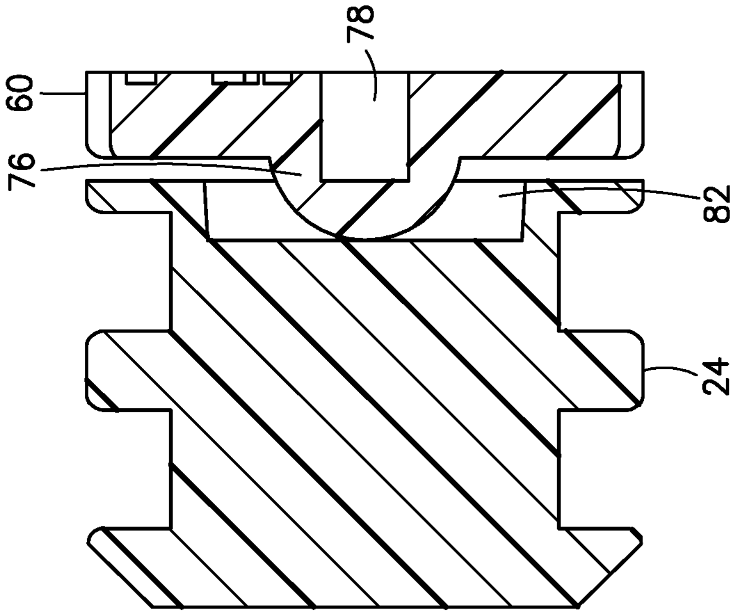
Figure 11:
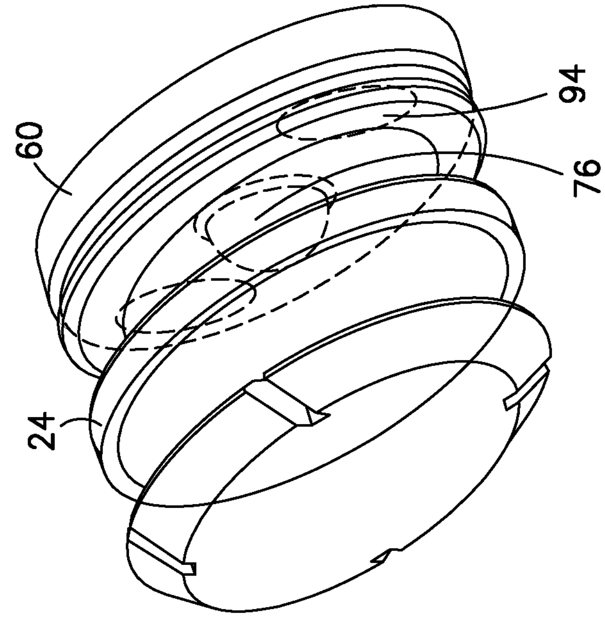
FIG. 11 is a perspective view of an example plunger and pusher constructed in accordance with an example embodiment.

FIG. 11 is a prospective view of the plunger 24 and pusher 60 showing the plunger with the pusher protrusion 76 in phantom. FIGS. 4G and 4H are cross-section side views of two different example embodiments of a plunger recess 82. In FIG. 4G, the distal end of the recess 82 is flat. In FIG. 4H, the distal end of the recess 82 has a pocket recess 84.

When the pusher 60 and plunger 24 come together, they act with some features similar to a mechanical ball joint, which is a mechanism used to allow for free rotation in multiple planes while restricting all translation. In accordance with example embodiments of the technical solution described herein, the joint is made to allow rotation with no constraint on translation. Therefore, the pusher 60 can transmit axial motion (i.e., minus any cosine-like effects from wobble) without inducing tilting or wobble in the plunger 24. The axial centering of the pusher 60 is achieved by its perimeter shape which follows the contour of the barrel-type reservoir 22 where it is moving.

In accordance with the technical solution described herein, the plunger can be self-stable when pushed, i.e. moves in the axial direction only when pushed upon, because of the ball or dome-like feature 76 pushing the plunger. The ball or dome-like feature 76 significantly reduces the amount of torque induced by non-axial forces or moments, especially when the pusher 60 is also sized to stay generally centered within the reservoir 22 by virtue of its perimeter shape. Since the drive mechanism 30 behind the pusher 60 cannot be fully constrained (i.e., without loss of axial space) to not wobble off axis, the pusher 60 can wobble to the extent allowed by its perimeter shape while pushing the plunger 24 but without transferring the direct wobble motion.

It is important to prevent rotation of the distal screw of the drive mechanism 30 and imparting of any drive mechanism rotation to the pusher 60. Anti-rotation is achieved with an elliptical cross-section reservoir 22, for example, and the pusher 60 being similarly shaped so that when the drive screw connected to it experiences a torque, the pusher 60 cannot rotate and the torque is thus transmitted to the next screw in the drive mechanism 30, which starts rotation and extension of the nested telescopic screws in the drive mechanism.

In accordance with another example embodiment and as stated above in connection with FIG. 2, the front face of the pusher 60 can be configured as a flat surface with no protrusion 76 that has essentially full face contact with the rear facing surface of the plunger 24. With reference to FIGS. 6A and 6B, which are respective side and cross-sectional side views of the fluid delivery device, the pusher 60 can be configured as a disk with a recess 78 that may or may not extend through the entire thickness of the pusher 60. As shown in FIG. 6B, any portion of the inner screw key feature (e.g., keying feature 80 shown in FIG. 5) that extends beyond the thickness of the disk can be received in the plunger recess 82.

Figure 7B:
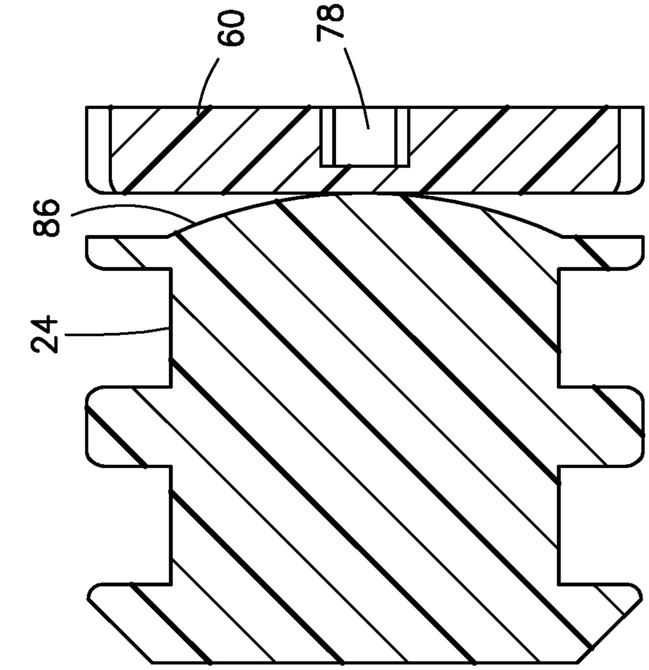
FIGS. 7A and 7B are respective side and cross-section side views of an example plunger and pusher constructed in accordance with example embodiments.
Figure 7A:
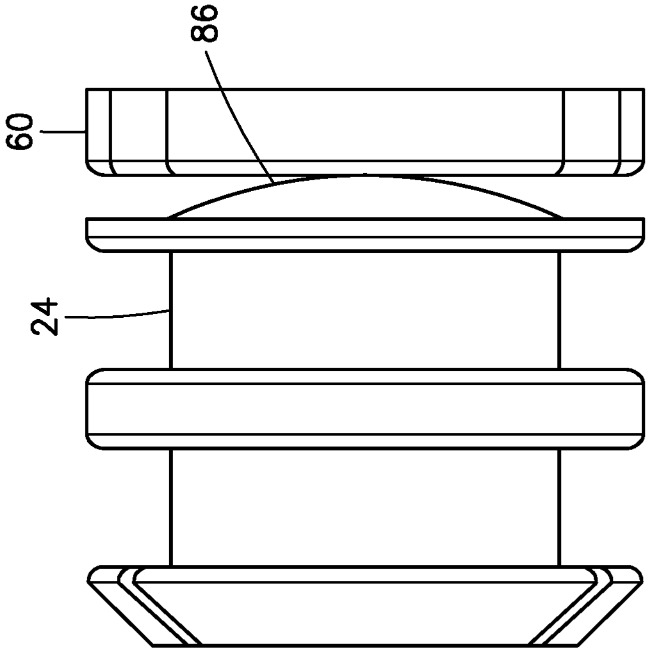

In accordance with another example embodiment, the front face of the pusher 60 is configured as a flat surface, and the recess 78 for a key feature (e.g., keying feature 80 shown in FIG. 5) does not extend through the entire thickness of the pusher 60. As shown in FIGS. 7A and 7B, the rear face of the plunger 24 is provided with a dome-like or half-spherical protrusion 86 to achieve a ball joint-type mechanism relative to the flat front face of the pusher 60 to allow for free rotation in multiple planes and thereby prevent the drive mechanism 30 and plunger 60 from imparting non-axial forces onto the plunger 24. In addition, the front face of the pusher can be provided with a recess to accommodate a portion of the plunger protrusion 86. This pusher 60 and plunger 24 coupling configuration allows for variable volume fill of a drug delivery device.

Figure 8B:
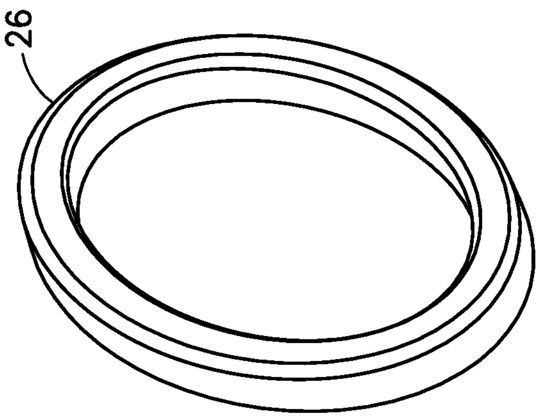
FIG. 8B is a perspective view of an example O-ring, in accordance with an example embodiment.
Figure 8A:
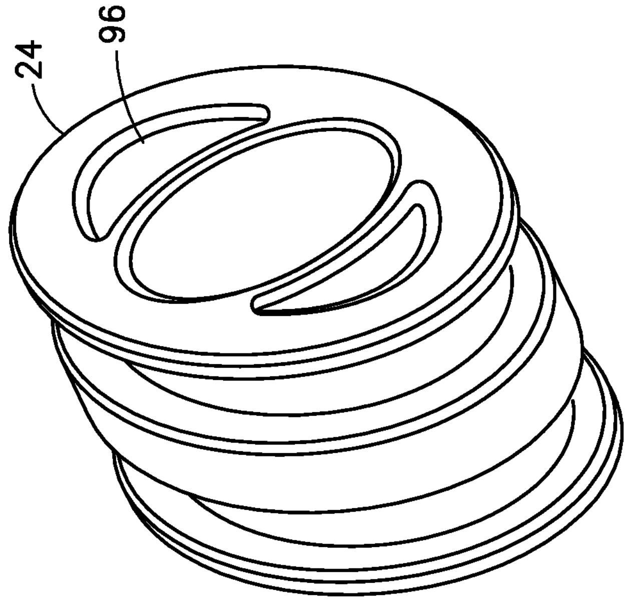
FIG. 8A is a perspective view of an example plunger without its O-rings.
Figure 9:
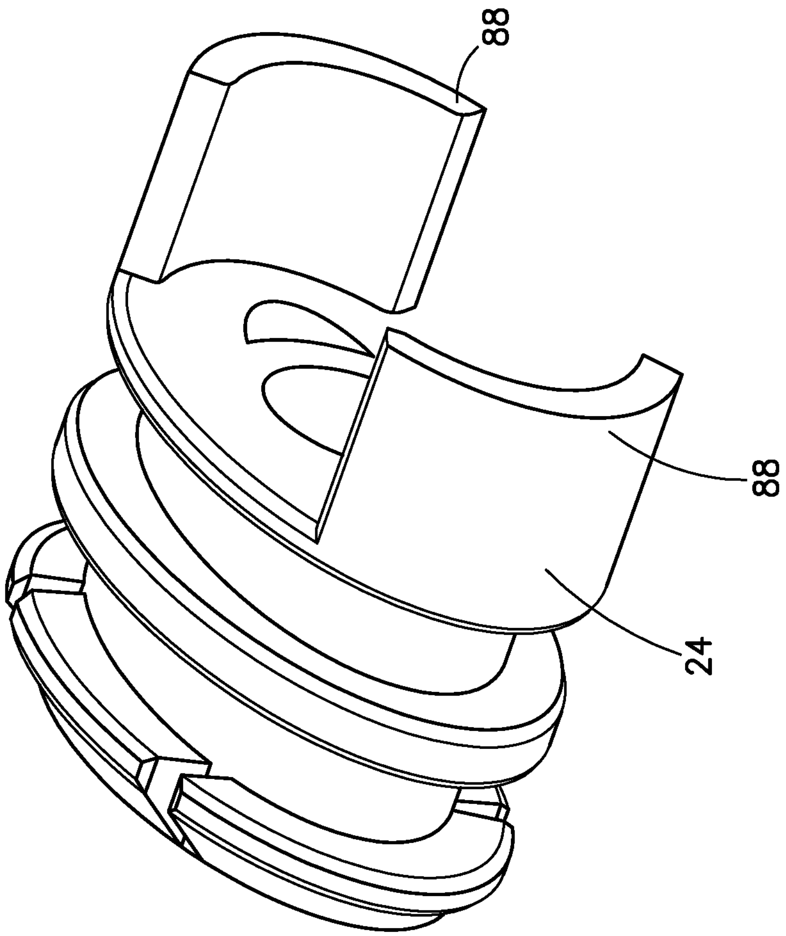
FIG. 9 is a perspective view of an example plunger constructed in accordance with an example embodiment.

FIGS. 8A and 8B provide, respectively, a perspective view of the plunger 24 without its O-rings 26, and a perspective view of an O-ring 26. In the example embodiment in FIGS. 6A and 6B, the pusher 60 and plunger 24 come into direct face-to-face contact which is a mechanical configuration that is more conducive to transmitting an off-axis motion to the driven plunger 24, resulting in dosing errors. To overcome transmission of off-axis motion to the plunger by the pusher 60, the plunger can be provided with wings 88 as shown in FIG. 9 to improve the axial movement stability and constrain as much as possible to axial motion only. The wings 88 can be integrally molded extensions along part of the plunger 24 perimeter that define a space in between them dimensioned to receive the disk-shaped pusher 60. The added length of the plunger 24 as a result of the wings 88 can be less desirable in terms of minimizing the form factor of the drug delivery device, and possibly contribute to more friction. Nonetheless, the wings can further stabilize the plunger 24 against non-axial motion from the pusher 60. In addition, the wings can be used with other pusher 60 and plunger 24 coupling configurations wherein a dome-like structure 76 or 86 is provided.

Figure 10B:
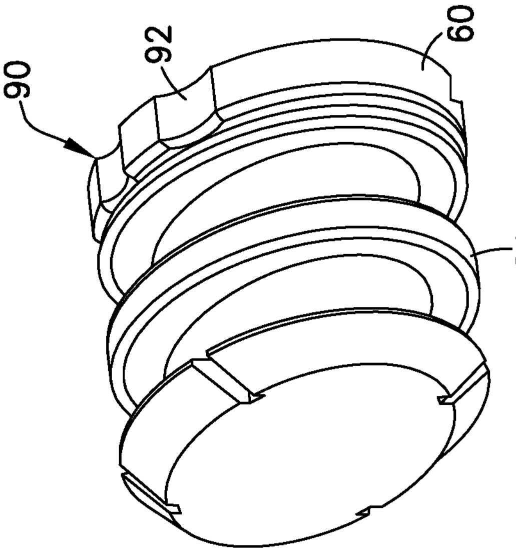
FIGS. 10A and 10B are perspective views of an example plunger and pusher constructed in accordance with an example embodiment.
Figure 10A:
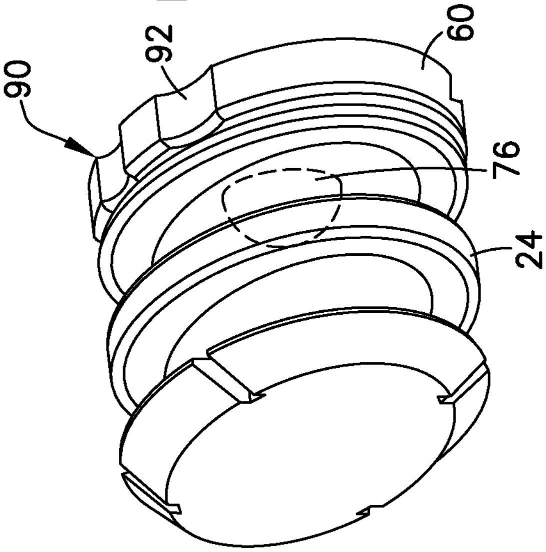
Figure 12A:
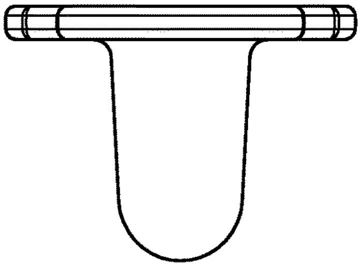
FIGS. 12A, 12B, 12C and 12D are, respectively, a perspective side view, a perspective front view, a perspective bottom view and a bottom view of a pusher constructed in accordance with an example embodiment.
Figure 12B:
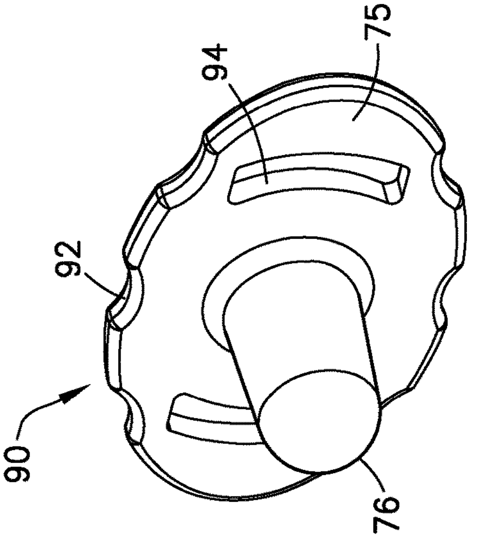
Figure 12C:
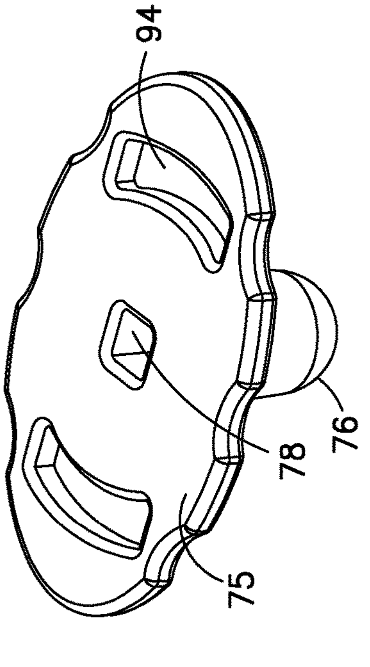
Figure 12D:
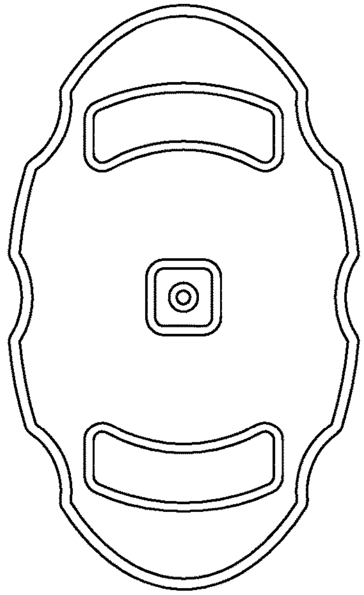

The pusher 60, and alternatively a cap on the reservoir 22 if employed, is provided with feature(s) to allow air venting. For example, an air venting feature can be provided along at least a portion 90 of the perimeter of the pusher 60 and be in the form of a scalloped edge 90 comprising notches 92. FIGS. 10A and 10B illustrate an example embodiment wherein a least a portion 90 of the pusher 60 perimeter is scalloped or otherwise provided with indents or notches 92. When notches 92 are provided on the perimeter of the pusher 60, these features 92 can be arranged to minimize axial translation friction by biasing design and tolerances for edges around a few of these features 92 to be more proud of the remaining notch edges (e.g., see FIG. 12B) so as to make first contact with the internal reservoir barrel face to prevent rotation. FIG. 11 illustrates an example embodiment wherein the pusher 60 is provided with one or more through holes 94 in a plate-like portion of the pusher. FIGS. 12A, 12B, are various views of another example pusher 60 having a scalloped edge portions with notches 92 and through holes 94. The plunger 24 can optionally be provided with through holes 96 (FIG. 8A) in its rear face for improved air evacuation between the pusher 60 and the plunger 24, if needed during filling and operation.

Figure 13A:
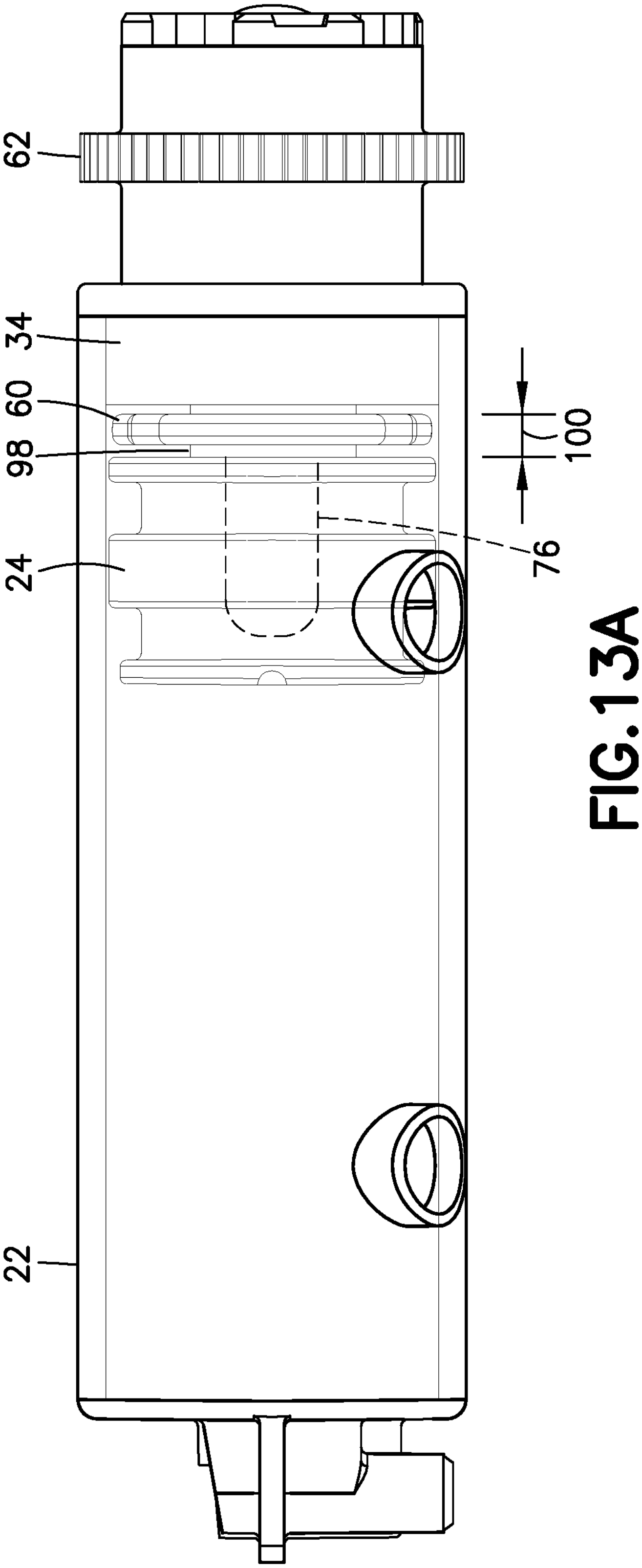
FIGS. 13A, 13B and 13C are, respectively, a side view, a perspective view and an exploded perspective view of a reservoir cap and pusher assembly constructed in accordance with an example embodiment.
Figure 13C:
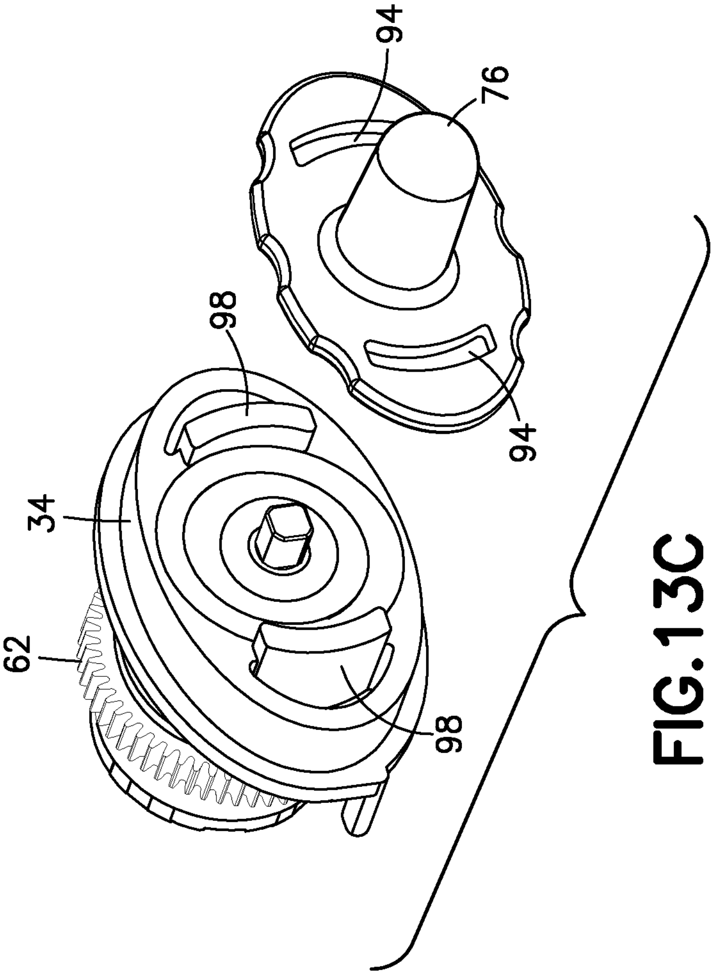
Figure 13B:
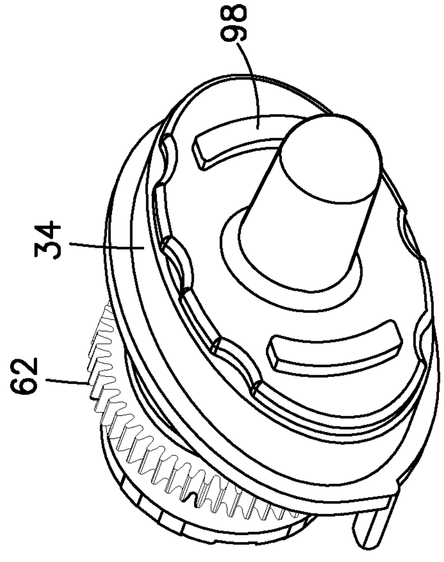

In accordance with another example embodiment shown in FIGS. 13A, 13B and 13C, the reservoir cap or gear anchor 34 is provided with protrusions 98 that stop filling motion of the plunger 24 if filling fully. The protrusions 98 are also depicted more clearly in FIGS. 3A and 3B in which the plunger 24 and pusher 60 are extended distally therefrom. The through holes or slots 94 in the pusher 60 cooperate with a feature such as the protrusions 98 incorporated in the gear anchor 34 to prevent the plunger 24 from bottoming out against the pusher 60 upon maximum filling and to thereby ensure a dispense operation starts with the plunger as flat as possible. These same cooperating features 94 and 98 also advantageously allow a minimum gap indicated at 100 of unloaded travel, that is, the thickness of the pusher 60 relative to the length of protrusion 98 extending beyond the front face of the gear anchor 34 and the distance traveled by the pusher 60 along the protrusion 98 when the pusher is fulling retracted by the drive mechanism 30. The gap 100 or unloaded travel can be used for dead band normalization in accordance with co-owned PCT/US2021/062562, filed Dec. 9, 2021 (e.g., monitor current to determine when the screw train starts traveling and then engages with the plunger in the filled configuration) to provide useful user feedback as well as device references for amount to be delivered.

As described above, in the case where a drive mechanism 30 employs two or more telescoping screws, the nature of the interface between the screws is that clearance is important to avoid binding, wear, or high torque. This clearance, however, allows for wobble when the screws extend with respect to each other. The tip of the most extended screw can therefore be significantly off axis compared to the axis of the reservoir 22 where the plunger 24 is to be pushed. If this distal end of the screw is off axis, the pushing force may be applied at a point that is not centered and may have significant angular components to it. In a high-precision device, such as a drug delivery pump, it is desired to have high dosing accuracy. In order to do so, the plunger 34 should move as consistently and repeatedly as possible, i.e., without any wobble.

The technical solution presented here significantly boosts dose accuracy of a pump with three screw stages to the point where it exceeds that of existing, predicate pumps which employ only two screw stages. It is to be understood that example embodiments of the technical solution described herein can be used advantageously with two screw stages as well as with other types of drive mechanisms. Thus, a fluid delivery device employing the technical solution has a performance advantage. For example, the technical solution can be employed in a wearable, low-cost drug delivery pump that can achieve high delivery precision throughout its life cycle and therefore use for Type 1 diabetes patients as well as Type II diabetes patients.

In addition to the anti-wobble plunger coupling configurations described herein with respect to example embodiments, different thread types and pitches may be used to further control the wobble of the plunger in the fluid delivery device. Also, the mating of the plunger 24 and pusher 60 realizes a joint that can be leveraged to make electrical confirmation of contact for reading by a sensor and use by a controller in the fluid delivery device to control and confirm dosing and status of the reservoir 22.

Example embodiments of the disclosure may address at least the above problems and/or disadvantages and other disadvantages not described above. Also, example embodiments are not required to overcome the disadvantages described above, and may not overcome any of the problems described above.

It will be understood by one skilled in the art that this disclosure is not limited in its application to the details of construction and the arrangement of components set forth in the above description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

The above-presented description and figures are intended by way of example only and are not intended to limit the illustrative embodiments in any way except as set forth in the following claims. It is particularly noted that persons skilled in the art can readily combine the various technical aspects of the various elements of the various illustrative embodiments that have been described above in numerous other ways, all of which are considered to be within the scope of the claims.

The invention claimed is:

1. A fluid delivery device with a syringe barrel having a reservoir chamber that can contain fluid and a plunger that translates within the chamber along a longitudinal reservoir axis thereof to expel fluid from the chamber and out of the syringe barrel via an outlet, the fluid delivery device further comprising:

a pusher dimensioned to translate within the barrel, the plunger having a front face directed toward the outlet and a rear face directed toward a front face of the pusher; and an extending mechanism coupled to a rear face of the pusher to controllably translate the pusher within the chamber along the longitudinal reservoir axis, the extending mechanism configured to extend the front face of the pusher to abut at least a portion of the rear face of the plunger to move the plunger;

wherein the perimeter of the syringe barrel, the plunger and the pusher have the same elliptical cross-sectional shape; and wherein the extending mechanism comprises telescopic nested screws rotated controllably to extend and retract the pusher, the rear face of the pusher is connected to a distal end of one of the nested screws, the distal end of the screw comprising an anti-rotation feature configured to cooperate with another anti-rotation feature provided on the rear face of the pusher.

2. The fluid delivery device of claim 1, wherein the pusher is configured as a plate and the extending mechanism is connected to a point on the rear face of the pusher that is centered with respect to the longitudinal reservoir axis.

3. The fluid delivery device of claim 2, wherein the rear face of the plunger is flat, and a majority of the front face of the pusher can abut the rear face of the plunger when the extending mechanism is moving the plunger via the pusher.

4. The fluid delivery device of claim 1, wherein the anti-rotation feature of the screw is a protrusion of selected shape, and the anti-rotation feature on the pusher is an indent having the selected shape to receive the protrusion.

5. The fluid delivery device of claim 1, wherein the front face of the pusher has a protrusion extending distally toward the rear face of the plunger.

6. The fluid delivery device of claim 5, wherein the protrusion has a half-spherical shape.

7. The fluid delivery device of claim 5, wherein the rear face of the plunger has a recess for receiving at least a portion of the protrusion.

8. The fluid delivery device of claim 7, wherein the protrusion and the recess are configured to cooperate together as a mechanical ball joint to reduce tilt of the plunger that could occur when translated by the extending mechanism driving pusher into the plunger.

9. The fluid delivery device of claim 7, wherein an innermost wall of the recess has a surface character that is flat, or contoured to accommodate at least part of the protrusion.

10. The fluid delivery device of claim 7, wherein the recess has a depth dimensioned to accommodate the full length of the protrusion to achieve direct contact of the front face of the pusher with the rear face of the plunger.

11. The fluid delivery device of claim 7, wherein the recess has a depth dimensioned to accommodate only a portion of the full length of the protrusion such that a gap exists between the front face of the pusher when driven into the rear face of the plunger by the extending mechanism.

12. The fluid delivery device of claim 1, wherein the pusher comprises air venting indents along at least a portion of its perimeter.

13. The fluid delivery device of claim 1, wherein the plunger has extensions from its rear face that form a receptacle to receive the pusher.

14. The fluid delivery device of claim 1, wherein the pusher comprises an aperture to rigidly receive one of the nested screws, the distal end of the screw protruding from the front side of the pusher, and the plunger comprising a recess to receive the protruding distal end therein.

15. The fluid delivery device of claim 1, wherein the plunger has a protrusion extending from its rear face toward the front face of the pusher, the protrusion contacting a point on the front face of the pusher that is centered with respect to the longitudinal reservoir axis.

16. The fluid delivery device of claim 1, wherein a contact is provided to at least one of the plunger and the pusher and a sensor and controller are provided in the fluid delivery device, the sensor being operable to provide a contact signal to the controller when the plunger and the pusher contact each other.

17. The fluid delivery device of claim 1, wherein the pusher comprises holes extending from its front face to its rear face, and a front face of the extending mechanism is provided with protrusions received in the holes on the pusher when the extending mechanism fully retracts the pusher.

* * * * *